United States Patent
Lin

(10) Patent No.: US 9,438,264 B1
(45) Date of Patent: Sep. 6, 2016

(54) HIGH-SPEED CAPACITIVE DIGITAL-TO-ANALOG CONVERTER AND METHOD THEREOF

(71) Applicant: Realtek Semiconductor Corp., Hsinchu (TW)

(72) Inventor: Chia-Liang (Leon) Lin, Fremont, CA (US)

(73) Assignee: REALTEK SEMICONDUCTOR CORP., Hsinchu (TW)

( * ) Notice: Subject to any disclaimer, the term of this patent is extended or adjusted under 35 U.S.C. 154(b) by 0 days.

(21) Appl. No.: 14/849,646

(22) Filed: Sep. 10, 2015

(51) Int. Cl.
*H03M 1/66* (2006.01)

(52) U.S. Cl.
CPC ..................................... *H03M 1/66* (2013.01)

(58) Field of Classification Search
CPC .......... H03M 1/66; H03M 1/46; H03M 3/50; H03M 2201/52; H03M 2201/122; H03M 2201/13
USPC ......................................... 341/144, 145, 150
See application file for complete search history.

(56) References Cited

U.S. PATENT DOCUMENTS

| | | | |
|---|---|---|---|
| 8,957,803 B2* | 2/2015 | Balasubramaniam | H03M 1/0678 341/144 |
| 2012/0306676 A1* | 12/2012 | Balasubramaniam | H03M 1/0678 341/144 |
| 2014/0266838 A1* | 9/2014 | Dempsey | H03M 1/68 341/145 |

* cited by examiner

*Primary Examiner* — Jean B Jeanglaude
(74) *Attorney, Agent, or Firm* — McClure, Qualey & Rodack, LLP

(57) ABSTRACT

A circuit having a capacitor coupling a first circuit node to a second circuit node; a first switch network configured to couple the second circuit node to either a first reference voltage or a second reference voltage in accordance with a value of a logical signal; and a second switch network configured to couple the second circuit node to a third reference voltage when the logical signal undergoes a transition but decouple the second circuit node from the third reference voltage when the logical signal finishes the transition.

17 Claims, 4 Drawing Sheets

US 9,438,264 B1

HIGH-SPEED CAPACITIVE DIGITAL-TO-ANALOG CONVERTER AND METHOD THEREOF

BACKGROUND OF THE INVENTION

1. Field of the Invention

The present invention generally relates to digital-to-analog converters and more particularly to a digital-to-analog converters and associated methods.

2. Description of Related Art

Persons of ordinary skill in the art understand terms and basic concepts related to microelectronics that are used in this disclosure, such as "voltage," "current," "signal," "logical signal," "clock," "transistor," "MOS (metal-oxide semiconductor)," "PMOS (p-channel metal oxide semiconductor)," "NMOS (n-channel metal oxide semiconductor)," "gate," "drain," "source," "threshold voltage," "circuit node," "power supply node," "ground node," and "switch." Terms and basic concepts like these are apparent to those of ordinary skill in the art and thus need not be explained in detail here.

Throughout this disclosure, a logical signal refers to a signal of two states: "high" and "low," which can also be re-phrased as "1" and "0." For brevity, a logical signal in the "high" ("low") state is simply stated as the logical signal is "high" ("low"), or alternatively, the logical signal is "1" ("0"). Also, for brevity, quotation marks may be omitted and the immediately above is simply stated as the logical signal is high (low), or alternatively, the logical signal is 1 (0), with the understanding that the statement is made in the context of describing a state of the logical signal.

A logical signal is said to be asserted when it is high. A logical signal is said to be de-asserted when it is low.

As is known, a digital-to-analog converter (DAC) receives a digital signal and outputs an analog signal, wherein the value of the analog signal represents a value of the digital signal. A capacitive DAC comprises a capacitor, a voltage of which represents an analog signal determined by a value of a digital signal. FIG. 1 shows a schematic diagram of a prior art capacitive DAC 100, which comprises: a capacitor 120 and a switch network 110. A first end 121 of the capacitor 120 couples to an output node 101, and a second end 122 of the capacitor 120 couples to an input node 113. The switch network 110 comprises a PMOS (p-channel metal oxide semiconductor) transistor 111 and a NMOS (n-channel metal oxide semiconductor) transistor 112, and is controlled by a digital signal DD, which is a logical signal. When the digital signal DD is asserted (de-asserted), the NMOS (PMOS) transistor 112 (111) is turned on while the PMOS (NMOS) transistor 111 (112) is turned off, and the input node 113 is coupled to a low (high) reference voltage VRL (VRH) via the NMOS (PMOS) transistor 112 (111). The high reference voltage VRH is higher than the low reference voltage VRL, and therefore a voltage at the output node 101 is higher when the digital signal DD is de-asserted than when the digital signal DD is asserted. The voltage at the output node 101 thus represents a value of the digital signal DD.

Implementation details of FIG. 1 (for instance, the source, the gate, and the drain of the PMOS transistor 111 couple to the high reference voltage VRH, the digital signal DD, and the input node 113, respectively) will be understood to those of ordinary skill in the art and thus are not explained here. Upon a change of value of the digital signal DD, a switching activity takes place within the switch network 110. For a high-speed application, the voltage at the output node 101 must change quickly in response to the change of value of the digital signal DD. To enable the voltage at the output node 101 to change quickly in response to a high-to-low (low-to-high) change of the value of the digital signal DD, a large sourcing (sinking) current IH (IL) must be provided from (to) the high (low) reference voltage VRH (VRL) via the PMOS (NMOS) transistor 111 (112). Although not explicitly shown in FIG. 1, the high reference voltage VRH and the low reference voltage VRL come from a respective reference voltage generation circuit. To allow a large sourcing or sinking current, the respective reference voltage generation circuit must have a high driving capability, as known by those of ordinary skill in the art.

What is desired is a high-speed DAC circuit that relaxes a requirement of a driving capability of a reference voltage generation circuit.

BRIEF SUMMARY OF THIS INVENTION

In an embodiment of the invention, a circuit comprises: a capacitor configured to couple a first circuit node to a second circuit node; a first switch network configured to couple the second circuit node to either a first reference voltage or a second reference voltage in accordance with a value of a logical signal; and a second switch network configured to couple the second circuit node to a third reference voltage when the logical signal undergoes a transition but decouple the second circuit node from the third reference voltage when the logical signal finishes the transition. In an embodiment, the first reference voltage is higher than the second reference voltage but not higher than the third reference voltage, and the transition is a high-to-low transition. In an alternative embodiment, the second reference voltage is lower than the first reference voltage but not lower than the third reference voltage, and the transition is a low-to-high transition.

In an embodiment, the second switch network comprises a serial network comprising a serial connection of a first MOS transistor of a first type and a second MOS transistor of a second type, wherein the first MOS transistor of the first type is controlled by the logical signal and configured to couple the third reference voltage to a third circuit node when the logical signal is of a first state, and the second MOS transistor of the second type is controlled by a substantially stationary voltage and configured to couple the third circuit node to the second circuit node when a difference between the substantially stationary voltage and a voltage of the second circuit node is larger than a threshold voltage of the second MOS transistor of the second type.

In an embodiment, a circuit comprises: a capacitor configured to couple a first circuit node to a second circuit node; a first switch network configured to couple the second circuit node to either a first reference voltage or a second reference voltage in accordance with a value of a logical signal; and a second switch network configured to couple the second circuit node to a third reference voltage when the logical signal undergoes a transition but decouple the second circuit node from the third reference voltage when the logical signal finishes the transition, wherein the second switch network comprises a serial connection of a switch device controlled by the logical signal and a valve device that automatically shuts off itself when the logical signal finishes the transition. In an embodiment, the switch device comprises a first MOS (metal oxide semiconductor) transistor of a first type controlled by the logical signal and configured to couple the third reference voltage to a third circuit node when the logical signal is in an enabling state, and the valve device comprises a second MOS transistor of a second type controlled by a substantially stationary voltage and configured to couple the third circuit node to the second circuit node when a difference between the substantially stationary voltage and a voltage of the second circuit node is larger than a threshold voltage of the second MOS transistor of the second type.

In an embodiment, a method comprises: incorporating a capacitor configured to couple a first circuit node to a second circuit node; incorporating a first switch network configured to couple the second circuit node to either a first reference voltage or a second reference voltage in accordance with a value of a logical signal; and incorporating a second switch network configured to temporarily couple the second circuit node to a third reference voltage when the logical signal is undergoing a transition and decouple the second circuit node from the third reference voltage when the transition is finished. In an embodiment, the first reference voltage is higher than the second reference voltage but not higher than the third reference voltage, and the transition is a high-to-low transition. In an alternative embodiment, the second reference voltage is lower than the first reference voltage but not lower than the third reference voltage, and the transition is a low-to-high transition. In an embodiment, the second switch network comprises a serial network comprising a serial connection of a first MOS transistor of a first type and a second MOS transistor of a second type. In an embodiment, the first MOS transistor of the first type is controlled by the logical signal and configured to couple the third reference voltage to a third circuit node when the logical signal is of a first state, and the second MOS transistor of the second type is controlled by a substantially stationary voltage and configured to couple the third circuit node to the second circuit node when a difference between the substantially stationary voltage and a voltage of the second circuit node is larger than a threshold voltage of the second MOS transistor of the second type.

DETAILED DESCRIPTION OF THIS INVENTION

The present invention relates to digital-to-analog converters. While the specification describes several example embodiments of the invention considered favorable modes of practicing the invention, it should be understood that the invention can be implemented in many ways and is not limited to the particular examples described below or to the particular manner in which any features of such examples are implemented. In other instances, well-known details are not shown or described to avoid obscuring aspects of the invention.

Throughout this disclosure, "VDD" denotes a power supply voltage, and "VSS" denotes a ground voltage; both notations are widely used and understood by persons in the prior art.

Figure 1:
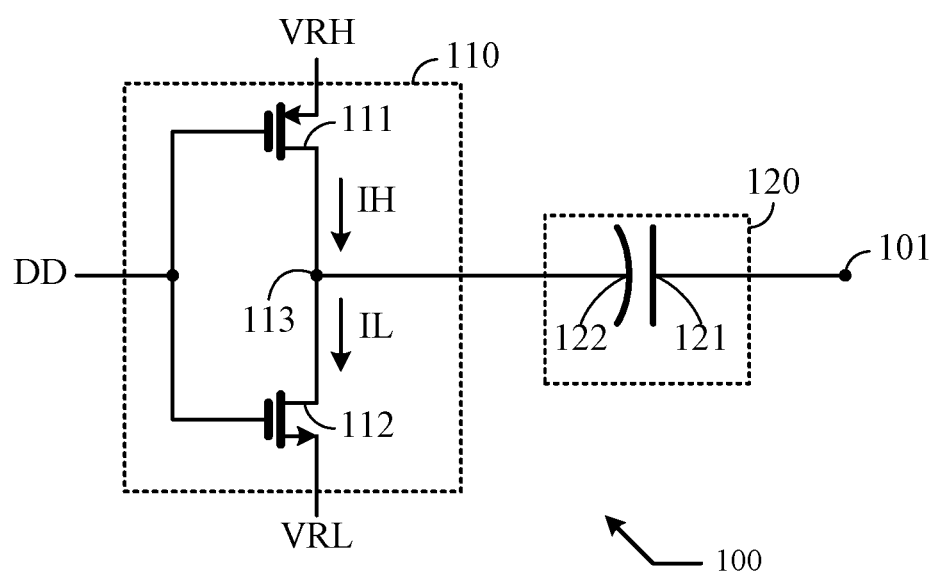
FIG. 1 shows a schematic diagram of a prior art capacitive DAC (digital-to-analog converter) circuit.
Figure 2:
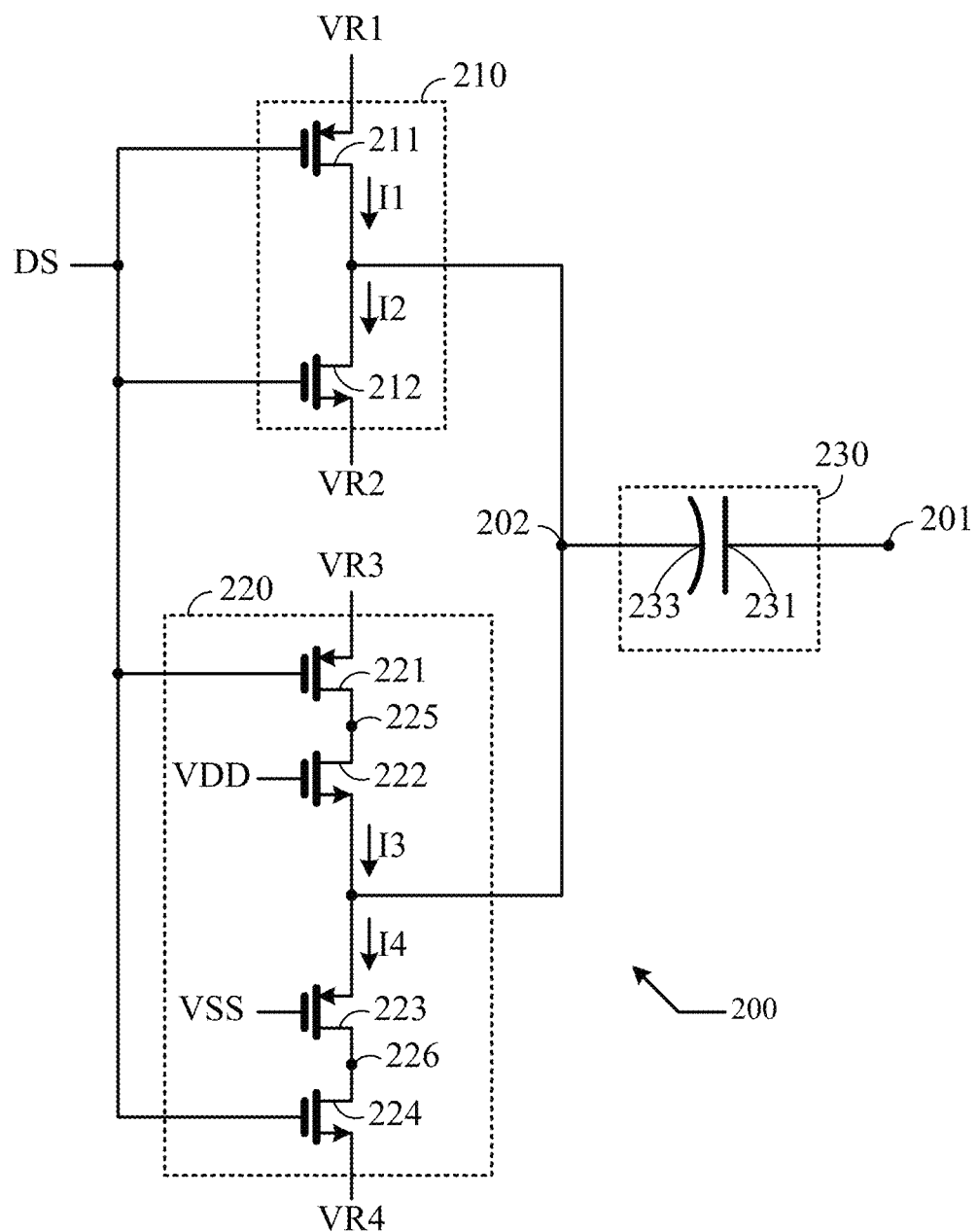
FIG. 2 shows a schematic diagram of a capacitive DAC (digital-to-analog converter) circuit in accordance with an embodiment of the present invention.

FIG. 2 shows a schematic diagram of a digital-to-analog converter (DAC) 200 in accordance with an embodiment of the present invention. DAC 200 comprises: a capacitor 230 configured to couple a first node 201 to a second node 202, a first switch network 210 configured to couple the second node 202 to either a first reference voltage VR1 or a second reference voltage VR2 in accordance with a value of a digital signal DS, and a second switch network 220 configured to conditionally couple the second node 202 to a third reference voltage VR3 or to a fourth reference voltage VR4 in accordance with the value of the digital signal DS and a state of a voltage at the second node 202. The first switch network 210 comprises a first PMOS transistor 211 and a first NMOS transistor 212. The second switch network 220 comprises a second PMOS transistor 221, a second NMOS transistor 222, a third PMOS transistor 223, and a third NMOS transistor 224. Here, the first reference voltage VR1 is higher than the second reference voltage VR2 but not higher than the third reference voltage VR3, while the second reference voltage VR2 is lower than the first reference voltage VR1 but not lower than the fourth reference voltage VR4. Persons of ordinary skill in the art will understand that DAC 200 of FIG. 2 is the same as DAC 100 of FIG. 1 except for having the second switch network 220. For differentiation purpose, the high reference voltage VRH, the low reference voltage VRL, and the digital signal DD in FIG. 1 are replaced by the first reference voltage VR1, the second reference voltage VR2, and the digital signal DS, respectively, in FIG. 2. The first switch network 210 in FIG. 2 is the same as the switch network 110 in FIG. 1 and thus not described again here.

For differentiation purpose, the sourcing current IH and the sinking current IL in FIG. 1 are replaced by a first current I1 and a second current I2, respectively. Upon a high-to-low (low-to-high) change of a value of the digital signal DS, a switching activity takes place, and the first (second) current I1 (I2) is sourced (sunk) from (to) VR1 (VR2) to (from) the second node 202 via the first PMOS (NMOS) transistor 211 (212) to change a voltage at the second node 202 and thus a voltage at the first node 201. The second switch network 220 of FIG. 2 is introduced to speed up the switching. Upon a high-to-low (low-to-high) change of a value of the digital signal DS, a third (fourth) current I3 (I4) is sourced (sunk) from VR3 (VR4) to (from) the second node 202 via the second (third) PMOS transistor 221 (223) and the second (third) NMOS transistor 222 (224). In an embodiment, the third reference voltage VR3 is higher than the first reference voltage VR1, and as a result, the third current I3 is larger than the first current I1. (That is, a higher voltage can source a larger current, as is understood by those of ordinary skill in the art and thus not explained in detail here.) In an embodiment, the fourth voltage VR4 is lower than the second reference voltage VR2, and as a result, the fourth current I4 is larger than the second current I2. (Again, a lower voltage can sink a larger current, as is well understood by those of ordinary skill in the art and thus not explained in detail here.)

The effect of the second switch network 220, however, is only temporary. By design, a threshold voltage of the second NMOS transistor 222 is larger in magnitude than a difference between the power supply voltage VDD and the first reference voltage VR1, and also a threshold voltage of the third PMOS transistor 223 is larger in magnitude than a voltage difference between the second reference voltage VR2 and the ground voltage VSS. A voltage of the second node 202 will be rising (falling) and approaching the first (second) reference voltage VR1 (VR2) after a high-to-low (low-to-high) change of the value of the digital signal DS. At some point, the voltage of the second node 202 rises (falls) too high (low) that a gate-to-source voltage of the second (third) NMOS (PMOS) transistor 222 (223) is smaller in magnitude than the threshold voltage of the second (third) NMOS (PMOS) transistor 222 (223), thus turning off the second (third) NMOS (PMOS) transistor 222 (223) and consequently shutting off the third (fourth) current I3 (I4). In other words, the second switch network 220 is effective only for a finite period of time after a change of value of the digital signal DS, and will not affect the end result of the DAC 200. That is, the DAC 200 of FIG. 2 is functionally equivalent to the DAC 100 of FIG. 1, but can be faster due to using the second switch network 220 to speed up a transition.

The second PMOS transistor 221 and the second NMOS 222 transistor form a first serial network configured to speed up a low-to-high transition of the voltage at the second node 202, while the third NMOS transistor 224 and the third PMOS transistor 223 form a second serial network configured to speed up a high-to-low transition of the voltage at the second node 202. The first serial network and the second serial network serve different purposes. The first serial network can be used when we seek to speed up the low-to-high transition of the voltage at the second circuit node 202, and is particularly effective when the third reference voltage VR3 is higher than the first reference voltage VR1. The second serial network can be used when we seek to speed up the high-to-low transition of the voltage at the second circuit node 202, and is particularly effective when the fourth reference voltage VR4 is lower than the second reference voltage VR2. The first serial network may be removed, if it is not sought to speed up the low-to-high transition of the voltage at the second circuit node 202. Likewise, the second serial network may be removed if it is not sought to speed up the high-to-low transition of the voltage at the second circuit node 202.

In a special case where the first reference voltage VR1 is the same as the power supply voltage VDD, the first serial network, which comprises the second PMOS transistor 221 and the second NMOS transistor 222, is not very effective and thus can be removed. In a special case where the second reference voltage VR2 is the same as the ground voltage VSS, the second serial network, which comprises the third PMOS transistor 223 and the third NMOS transistor 224, is not very effective and thus can be removed.

Both the second NMOS transistor 222 and the third PMOS transistor 223 function as a "valve." The second NMOS transistor 222 allows the third current I3 to flow from circuit node 225 to the second circuit node 202 when the voltage at the second circuit node 202 is low, but will automatically shut off itself when the voltage at the second circuit node 202 rises too high, thus functioning as a valve. Likewise the third PMOS transistor 223 allows the fourth current I4 to flow from the second circuit node 202 to circuit node 226 when the voltage at circuit node 202 is high, but will be automatically shut off itself when the voltage at the second circuit node 202 falls too low, thus functioning as a valve.

By way of example but not limitation: VDD is 1.05V; VR1 is 0.8V; VR3 is 1.05V; VSS is 0V; VR2 is 0V; VR4 is 0V; the third PMOS transistor 223 and the third NMOS transistor 224 are not used (since VR2 is the same as VR4, and thus the third PMOS transistor 223 and the third NMOS transistor 224 are not very effective, as explained earlier); the width/length is 9.6 µm/30 nm for both the first PMOS transistor 211 and the second PMOS transistor 221; the width/length is 8 µm/30 nm for both the first NMOS transistor 212 and the second NMOS transistor 222; the capacitor 230 is 400 fF; a capacitive load at the first node 201 (not shown in FIG. 2 but is clear to those of ordinary skill in the art) is 400 fF; and VR1 is provided by a reference voltage generation circuit that has 500 Ohm output resistance. For purpose of comparison, referring to FIG. 1: VRH is 0.8V; VRL is 0V; the width/length is 19.2 µm/30 nm for the PMOS transistor 111; the width/length is 16 µm/30 nm for the NMOS transistor 112; the capacitor 120 is 400 fF; a capacitive load at the output node 101 (not shown in FIG. 1 but is clear to those of ordinary skill in the art) is 400 fF; and VRH is provided by a reference voltage generation circuit that has 500 Ohm output resistance. Note that the PMOS transistor 111 and the NMOS transistor 112 are intentionally doubled for a fair comparison so that both the DAC 200 of FIG. 2 and the DAC 100 of FIG. 1 have the same total sizes of PMOS transistors.

Figure 3:
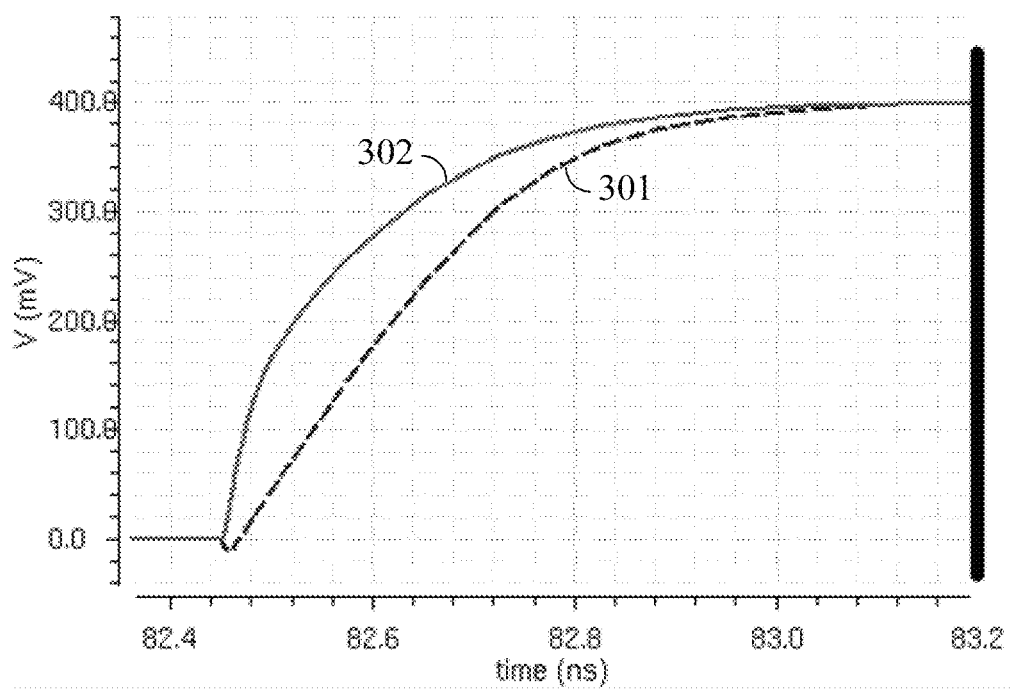
FIG. 3 shows a simulation result of a comparison between a prior art DAC of FIG. 1 and a DAC of FIG. 2.

A simulation result is shown in FIG. 3. Here, there are two traces 301 and 302. Trace 301 is a voltage at the output node 101 of FIG. 1, and trace 302 is a voltage at the first node 201 of FIG. 2, both responding to a high-to-low change of a respective digital signal (i.e., the digital signal DD in FIG. 1 and digital signal DS in FIG. 1). It is clear that the DAC 200 of FIG. 2 is much faster than the DAC 100 of FIG. 1.

The DAC 200 of FIG. 2 is a single-bit DAC. Persons of ordinary skill in the art will understand that, a multiple-bit digital-to-analog converter can be constructed using a combination of a plurality of single-bit digital-to-analog converters, and therefore a multiple-bit embodiment for the present invention need not be separately and explicitly shown here.

Figure 4:
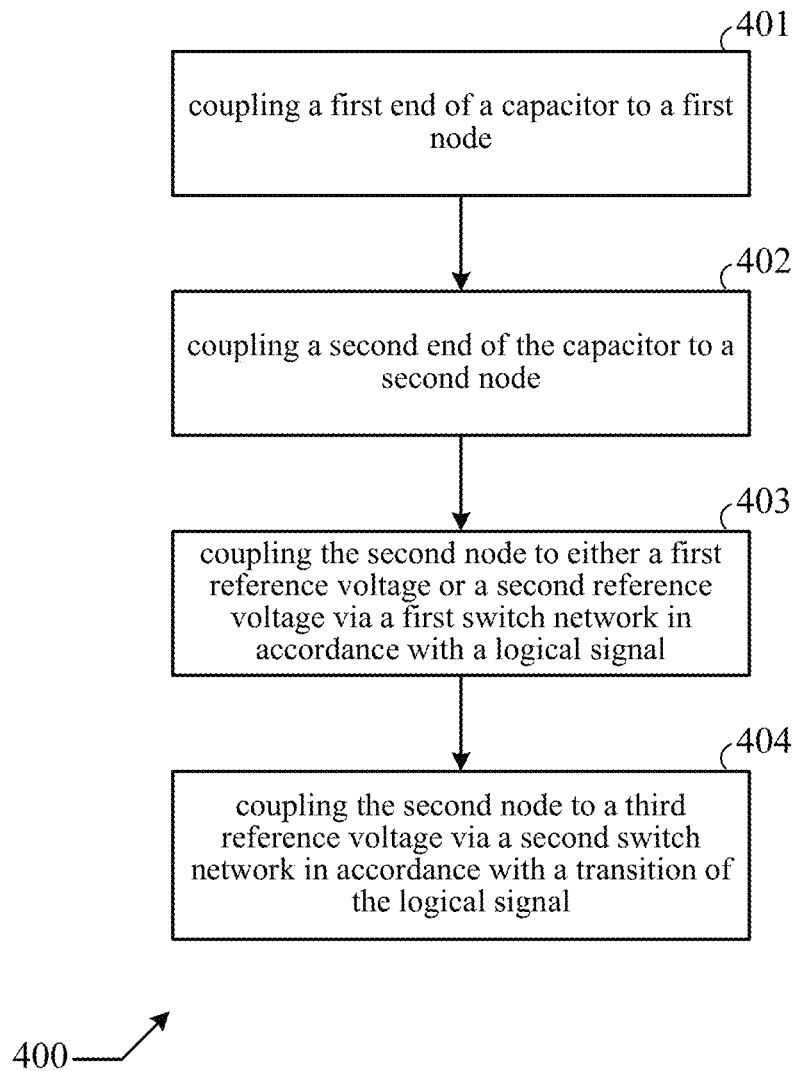
FIG. 4 shows a flow diagram of a method in accordance with an embodiment of the present invention.

FIG. 4 shows a flow diagram of a method 400 in accordance with an embodiment of the present invention. The method 400 comprises: coupling a first end of a capacitor to a first node (step 401); coupling a second end of the capacitor to a second node (step 402); coupling the second node to either a first reference voltage or a second reference voltage via a first switch network in accordance with a logical signal (step 403); and coupling the second node to a third reference voltage via a second switch network in accordance with a transition of the logical signal (step 404).

Persons skilled in the art will readily observe that numerous modifications and alterations of the device and method may be made while retaining the teachings of the invention. Accordingly, the above disclosure should be construed as limited only by the metes and bounds of the appended claims, and not by the embodiments specifically described in the specification.

What is claimed is:
1. A circuit comprising:
   a capacitor coupling a first circuit node to a second circuit node;
   a first switch network circuit coupling the second circuit node to either a first reference voltage or a second reference voltage in accordance with a value of a logical signal; and
   a second switch network circuit coupling the second circuit node to a third reference voltage when the logical signal undergoes a transition but decouple the second circuit node from the third reference voltage when the logical signal finishes the transition.
2. The circuit of claim 1, wherein the first reference voltage is higher than the second reference voltage but not higher than the third reference voltage, and the transition is a high-to-low transition.

3. The circuit of claim 1, wherein the second reference voltage is lower than the first reference voltage but not lower than the third reference voltage, and the transition is a low-to-high transition.

4. The circuit of claim 1, wherein the second switch network comprises a serial network comprising a serial connection of a first MOS (metal oxide semiconductor) transistor of a first type and a second MOS transistor of a second type, wherein the first MOS transistor of the first type is controlled by the logical signal and coupling the third reference voltage to a third circuit node when the logical signal is of a first state, and the second MOS transistor of the second type is controlled by a substantially stationary voltage and coupling the third circuit node to the second circuit node when a difference between the substantially stationary voltage and a voltage of the second circuit node is larger than a threshold voltage of the second MOS transistor of the second type.

5. The circuit of claim 4, wherein: the first reference voltage is higher than the second reference voltage but not higher than the third reference voltage, the substantially stationary voltage is a power supply voltage, the first MOS transistor of the first type is a PMOS (p-channel metal oxide semiconductor) transistor, and the second MOS transistor of the second type is a NMOS (n-channel metal oxide semiconductor) transistor.

6. The circuit of claim 4, wherein: the second reference voltage is lower than the second reference voltage but not lower than the third reference voltage, the substantially stationary voltage is a ground voltage, the first MOS transistor of the first type is a NMOS (n-channel metal oxide semiconductor) transistor, and the second MOS transistor of the second type is a PMOS (p-channel metal oxide semiconductor) transistor.

7. The circuit of claim 5, wherein the first switch network comprises a first PMOS (p-channel metal oxide semiconductor) transistor controlled by the logical signal and coupling the first reference voltage to the second circuit node when the logical signal is de-asserted and a first NMOS (n-channel metal oxide semiconductor) transistor controlled by the logical signal and configured to couple the second reference voltage to the second circuit node when the logical signal is asserted.

8. A circuit comprising:
a capacitor coupling a first circuit node to a second circuit node;
a first switch network circuit coupling the second circuit node to either a first reference voltage or a second reference voltage in accordance with a value of a logical signal; and
a second switch network circuit coupling the second circuit node to a third reference voltage when the logical signal undergoes a transition but decouple the second circuit node from the third reference voltage when the logical signal finishes the transition, wherein the second switch network comprises a serial connection of a switch device controlled by the logical signal and a valve device that automatically shuts off itself when the logical signal finishes the transition.

9. The circuit of claim 8, wherein the switch device comprises a first MOS (metal oxide semiconductor) transistor of a first type controlled by the logical signal and coupling the third reference voltage to a third circuit node when the logical signal is in an enabling state, and the valve device comprises a second MOS transistor of a second type controlled by a substantially stationary voltage and coupling the third circuit node to the second circuit node when a difference between the substantially stationary voltage and a voltage of the second circuit node is larger than a threshold voltage of the second MOS transistor of the second type.

10. A method comprising:
incorporating a capacitor coupling a first circuit node to a second circuit node;
incorporating a first switch network circuit coupling the second circuit node to either a first reference voltage or a second reference voltage in accordance with a value of a logical signal; and
incorporating a second switch network circuit temporarily coupling the second circuit node to a third reference voltage when the logical signal is undergoing a transition and decouple the second circuit node from the third reference voltage when the transition is finished.

11. The method of claim 10, wherein the first reference voltage is higher than the second reference voltage but not higher than the third reference voltage, and the transition is a high-to-low transition.

12. The method of claim 10, wherein the second reference voltage is lower than the first reference voltage but not lower than the third reference voltage, and the transition is a low-to-high transition.

13. The method of claim 10, wherein the second switch network comprises a serial network comprising a serial connection of a first MOS transistor of a first type and a second MOS transistor of a second type.

14. The method of claim 13, wherein the first MOS transistor of the first type is controlled by the logical signal and coupling the third reference voltage to a third circuit node when the logical signal is of a first state, and the second MOS transistor of the second type is controlled by a substantially stationary voltage and coupling the third circuit node to the second circuit node when a difference between the substantially stationary voltage and a voltage of the second circuit node is larger than a threshold voltage of the second MOS transistor of the second type.

15. The method of claim 10, wherein the second switch network comprises a serial network comprising a switch device and a valve device.

16. The method of claim 15, wherein the switch device is controlled by the logical signal and couples the third reference voltage to a third circuit node when the logical signal is in an enabling state.

17. The method of claim 16, wherein the valve device is controlled by a substantially stationary voltage and couples the third circuit node to the second circuit node when a difference between the substantially stationary voltage and a voltage of the second circuit node is larger than a threshold voltage of the valve device.

* * * * *